(12) United States Patent
Ramsay et al.

(10) Patent No.: US 7,297,530 B2
(45) Date of Patent: Nov. 20, 2007

(54) DEVICE FOR USE IN MONITORING A SWAB TECHNIQUE

(75) Inventors: Catherine Mary Ramsay, Cowbridge (GB); William John Simpson, Lingfield (GB)

(73) Assignee: Biotrace Limited (GB)

( * ) Notice: Subject to any disclaimer, the term of this patent is extended or adjusted under 35 U.S.C. 154(b) by 341 days.

(21) Appl. No.: 10/816,659

(22) Filed: Apr. 1, 2004

(65) Prior Publication Data

US 2005/0221471 A1    Oct. 6, 2005

(51) Int. Cl.
*C12M 1/34*    (2006.01)
(52) U.S. Cl. .................. 435/287.4; 435/30; 435/31; 435/287.8
(58) Field of Classification Search ............. 435/287.4, 435/30, 31, 287.8
See application file for complete search history.

(56) References Cited

U.S. PATENT DOCUMENTS 3,915,806 A * 10/1975 Horlach .................. 435/307.1
4,963,325 A    10/1990 Lennon et al.
5,403,741 A *  4/1995 Holbrook ................. 435/288.2
6,610,312 B2 * 8/2003 Farrell et al. ............... 424/401

FOREIGN PATENT DOCUMENTS

| EP | 0 171 150 A2 | | 2/1986 |
|----|----|----|----|
| EP | 0 915 336 A2 | | 5/1999 |
| EP | 0 916 405 A2 | | 5/1999 |
| GB | 1298069 | * | 4/2003 |
| WO | WO 93/19363 | | 9/1993 |
| WO | WO 97/06436 | | 2/1997 |
| WO | WO 98/48280 | | 10/1998 |
| WO | WO 98/50778 | | 11/1998 |
| WO | WO 98/56568 | | 12/1998 |
| WO | WO 99/33714 | | 8/1999 |
| WO | WO 00/54029 | | 9/2000 |

* cited by examiner

*Primary Examiner*—Ralph Gitomer
(74) *Attorney, Agent, or Firm*—Fulwider Patton LLP

(57) ABSTRACT

A device for use in monitoring a swab method, the device includes a first substrate substantially adjacent a second substrate, the first substrate and the second substrate having disposed therebetween a test material.

18 Claims, 1 Drawing Sheet

DEVICE FOR USE IN MONITORING A SWAB TECHNIQUE

FIELD OF THE INVENTION

The present invention is concerned with a device suitable for use in determining the accuracy of a swab technique.

BACKGROUND OF THE INVENTION

Various tests are available that can be used to assess the cleanliness of a surface. Such tests include those based on the detection of ATP using the firefly luciferase reaction, tests based on the detection of protein using colorimetry, tests based on the detection of micro-organisms using microbiological culture techniques, and tests based on detection of micro-organisms using immunochemical techniques. Surfaces can be sampled using either a swab device, or by direct contact with an agar medium.

Although the above tests are useful in the detection of a contaminated surface, they are typically prone to errors. These errors may be due to the performance of the measurement apparatus (a light detection device, such as a luminometer, colour detection by human assessor, or test result interpretation by human assessor).

It is also believed that errors may be due to variations in the assay conditions, for example being caused by assay temperature. Errors may also be due to the detection "reagents" used in the test systems, including firefly luciferase reagents for ATP, colorimetric reagents for protein detection, microbiological media for bacteriological analysis etc. For example, abused or badly stored reagents can give rise to false-positive or false-negative results.

Errors may also arise due to differences in sampling procedure. For example, "swabs" are often used for sample collection in such hygiene assays. These can give rise to variation due to the presence or absence of extraction agents and/or surface active components.

Furthermore, errors can arise due to differences in operator technique during the performance of the assay itself. Although this may be due to an error on the part of the operator, it is more common that the variance in performance is a result of subtle differences in technique.

All of the above sources of potential error ultimately lead to a reduction in confidence in the validity of such test results. In the case of safety critical applications there are significant consequences if a set of invalid results are generated.

There are a number of different methods for dealing with the inherent variability of surface hygiene tests. Such methods include:

1. Use of chemical standards (such as the use of solutions of ATP to calibrate ATP tests) (Jago, P H, Stanfield, G, Simpson, W J & Hammond, J R M 1989. In ATP Bioluminescence: Rapid Methods in Microbiology, Society of Applied Microbiology Technical Series, Vol. 26, Stanley P E et al [eds] pp 53-61). These can be applied in two ways. In the external calibration technique, the test response is compared to that obtained in the presence of known concentrations of the analyte. In the internal calibration technique, a known amount of analyte is added to the test after measurement of the sample signal. The ratio of the signal from the test sample to that of the standard can be used to calculate the amount of analyte present in the sample.

2. Use of a light sensitive derivative of the analyte to assure test performance. This is the basis of the Photo-Quant® technique for assay calibration (Method for calibrating chemical assays, PCT/GB95/00794);

3. Use of low level light emitting devices to assure the performance of instrumentation, or use of coloured cards to act as an aid to the judgment (by eye) of calorimetric tests etc. For example, radioactive material employing a scintillant are employed in the Biolink light standards (Leaback, D H, Easy-to-use light standards as aids to luminometry, Szalay, AA et al [Eds], pp 33-37, Bioluminescence of the VII International Symposium on Bioluminescence and Chemiluminescence, John Wiley & Son, Chichester 1993).

Whilst these methods are useful in some circumstances, there are a number of limitations. All of the approaches identified above are limited by the fact that they do not respond to differences in operator swab technique. Faulty sampling techniques (which may include failure to swab the required area, or failure to apply sufficient pressure during the swabbing process) can lead to low results (or even negative results).

SUMMARY OF THE INVENTION

It is therefore an aim of the present invention to alleviate at least some of the disadvantages highlighted above.

It is also an aim of the present invention to provide a standard surface for use in the monitoring of swab technique in an analytical method.

It is a further aim of the present invention to provide a method of monitoring swab technique.

Therefore, according to a first aspect of the present invention, there is provided a device for use in monitoring a user's technique of using a swab, the device includes a first substrate substantially adjacent a second substrate, the first substrate and the second substrate having disposed therebetween a test material.

Advantageously, the test material includes a predetermined amount of test analyte. The analyte may include ATP, a protein, other chemical materials (such as adenosine diphosphate (ADP), adenosine monophosphate (AMP) pyrophosphate (PPi), guanosine triphosphate (GTP), guanosine diphosphate (GDP), guanosine monophosphate (GMP), cytidine triphosphate (CTP), cytidine diphosphate (CDP), cytidine monophosphate (CMP), deoxyribonucleic acid (DNA), ribonucleic acid (RNA), various minerals (including Ca, Zn, Mg, Mn and Co), sugars (including lactose, glucose and maltose), lipids and fatty acids, microbial cell wall and cell membrane materials (such as peptidoglycan, techoic acid and lipopolysaccharides), enzymes (such as proteases, adenylate kinase, invertase, melibiase, and alkaline phosphatase) and/or a microorganism.

Advantageously, the test material is protected from the environment prior to use, thereby substantially reducing (or preferably substantially inhibiting) contamination of the test material by the external environment. The test material is typically disposed between the first substrate and the second substrate under aseptic conditions.

Preferably, the first substrate and the second substrate are sealed together substantially at their periphery so as to form a pouch or sachet, the test material preferably being substantially contained in the pouch. The first substrate and the second substrate may be sealed together by use of an hermetic bond, or the like. The bond may be formed by use of an adhesive, such as a polyurethane adhesive, alternatively, they be may joined together by use of heat sealing the first substrate and/or the second substrate or by a pressure sensitive adhesive. Heat sealing may include the use of heat sealing of a plastic polymer surface. It is also envisaged that the first substrate and the second substrate may be coextrusion laminated; the first substrate and/or the second substrate preferably being formed from materials such as ethylene vinyl acetate, ethylene methacylate or ethylene vinyl alcohol.

The first substrate and the second substrate may be of metal, including aluminum (such as aluminum foil), or a plastics material.

Each substrate may be of the same material. It is therefore envisaged that the first substrate and the second substrate are formed from the same sheet of material. In this embodiment, the sheet may be folded about a fold-line, the fold-line forming a sealed edge of the pouch. However, it is preferred that each substrate is of a different material.

It is particularly preferred that the first substrate and the second substrate have respective (internal) surfaces which have different wetting properties.

It is particularly desirable that the first substrate has a surface which is hydrophobic and the second substrate has a surface which is hydrophilic. Each substrate may be treated with, for example a polymer so as to form the hydrophilic and/or hydrophobic surface. However, it is also envisaged that each substrate may be of a hydrophilic or hydrophobic material. Advantageously, the test material disposed between the first substrate and the second substrate will preferentially wet the hydrophilic surface leaving the hydrophobic surface substantially unwetted.

This feature is particularly advantageous as, although in principle an equal volume of material should adhere to each substrate, in practice the surface is inconsistently wetted resulting in an unknown (or uneven) amount of analyte remaining on each substrate. Therefore, the use of different surfaces, one being hydrophilic and the other being hydrophobic, results in substantially all of the analyte being on the hydrophilic surface.

In this particular embodiment, it is preferred that the test material includes a hydrophilic surface enhancer, such as a detergent, which increases the probability of the test material wetting the hydrophilic surface as opposed to wetting the hydrophobic surface. Preferred hydrophilic surface enhancers include benzalkonium chloride, benzethonium chloride and chlorhexidine gluconate.

It is further desirable that the device (and therefore the test material) is stable prior to being used in the monitoring of, for example, swab technique. It is therefore preferred that the test material includes a stabilizing agent.

The stabilizing agent may include a chelating agent when the test material includes ATP (the non-enzymic breakdown of ATP is inhibited by chelating divalent cations). A preferred chelating agent includes ethylene diamine tetra-acetic acid (EDTA). In this particular embodiment, it is preferred that the test material has a low pH value (for example less than 7.0) so as to restrict base-catalyzed hydrolysis of ATP. In addition, it is preferred that the test material includes ADP when ATP is present in the test material (ADP has the advantage of reducing the hydrolysis of ATP to ADP).

It is preferred that when the test material includes a protein, the stabilizing agent includes a compound which reduces water availability (for example glycerol) therefore improving protein stability.

Preferably, when the test material includes a microorganism the stabilizing agent includes a quaternary ammonium detergent or biguanide, such as a benzethonium chloride or chlorhexidine gluconate, which advantageously acts as an inhibitor of enzyme action, and as a preservative against microbiological degradation.

A particularly preferred test material for use in the present invention, when the present invention is suitable for use in monitoring the swab method in an ATP assay and protein-based hygiene tests, includes a blend comprising:

| | |
|---|---|
| Glycerol | 50 g |
| Chlorhexidine gluconate | 2 g |
| Bovine serum albumin | 0.5 g |
| ATP | $0.18 \times 10^{-9}$ g |
| De-ionized water | 50 g |

According to a further aspect of the present invention, there is provided a method of manufacturing a device, for use in monitoring a swab technique, the method including providing a first substrate, applying a test material to a portion of the first substrate, covering at least the test material on the first substrate with a second substrate, and joining the second substrate to the first substrate so as to encapsulate the test material between the first substrate and the second substrate.

The device manufactured according to this aspect of the present invention is substantially as described herein before with reference to the first aspect of the present invention.

It is, however, envisaged that the device according to the first aspect of the present invention may be manufactured by methods known in the art of making sachets and/or pouches. Such methods include those disclosed in (but not limited to) U.S. Pat. No. 5,879,769, U.S. Pat. No. 5,445,821, U.S. Pat. No. 4,747,782, EP 1013193 and WO 9856568.

It is preferred that the test material is applied to the first substrate as a (relatively) dry, localized spot, (which is particularly preferred) or as a homogeneously applied film.

Typically, the test material has a thickness on the first substrate less than about 1 mm, preferably less than about 0.3 mm.

It is preferred that the first substrate includes a first release portion and the second substrate includes a second release portion, each release portion being arranged about a peripheral edge of the respective substrate. The first release portion being preferably substantially not connected to the second release portion.

According to yet a further aspect of the present invention, there is provided a method of monitoring a swab technique, which method includes:

a) providing a device comprising a first substrate substantially adjacent a second substrate, the first substrate and the second substrate having disposed therebetween a test material including a predetermined amount of an analyte;

b) swabbing the test material with a swab; and c) monitoring the amount of analyte present on the swab in step (b).

The device is substantially as described herein before.

The test material is typically disposed between the first substrate and the second substrate under aseptic conditions.

The amount of analyte present on the swab after step (b) may be monitored by methods known in the art. The mode of monitoring will, of course, be dependent on the analyte contained in the test material. The analyte may be monitored using, for example, apparatus currently sold by Biotrace Limited under the Trade Marks CLEAN-TRACE and PRO-TECT. Although it is envisaged that any suitable apparatus known to a person skilled in the art could be used.

The amount of analyte monitored on the swab after step (b) is compared to the amount of analyte present in the test material. The comparison provides an indication of how accurate the swab technique is. For example if monitoring the amount of analyte on the swab after step (b) identifies only about 50% of analyte present in the test material has been detected, the swab method may be considered as being unacceptable.

Other features and advantages of the invention will become apparent from the following detailed description, taken in conjunction with the accompanying drawings, which illustrate, by way of example, the features of the invention.

BRIEF DESCRIPTION OF THE DRAWINGS

The present invention will now be described with reference to the accompanying Figures, which are given by way of example only, wherein.

DETAILED DESCRIPTION OF THE INVENTION

Figure 1:
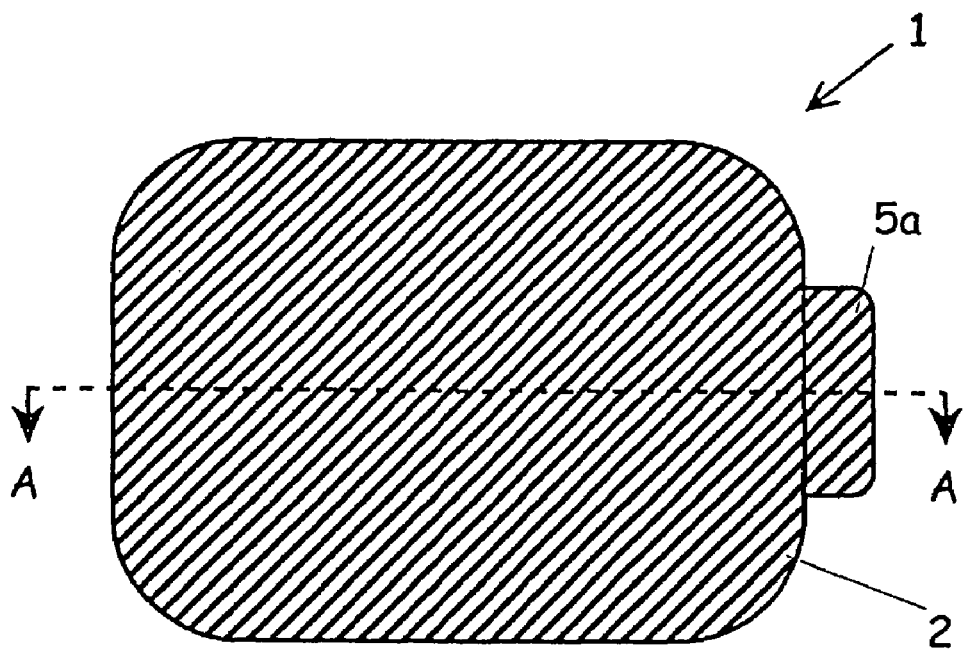
FIG. 1 represents a plan view of a device according to the present invention.
Figure 2:
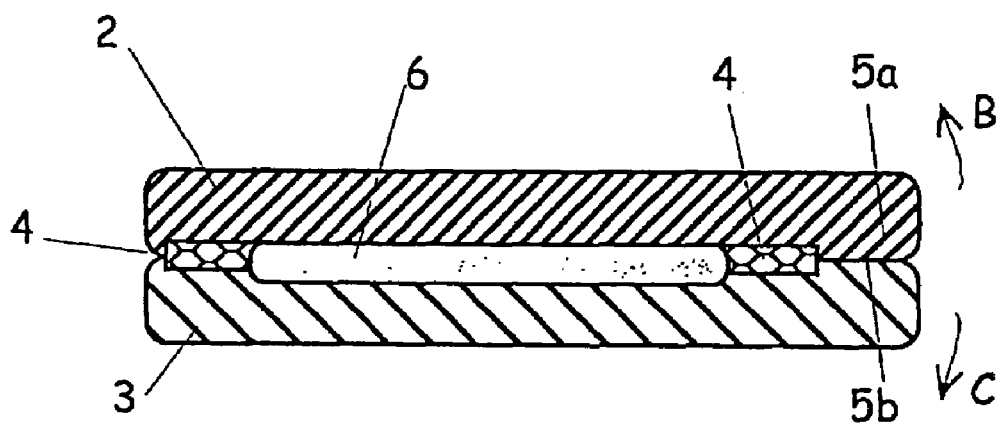
FIG. 2 represents a cross-sectional view along the line A-A of FIG. 1.

Referring to the figures, where like numerals have been used to represent like parts, there is provided a test sachet generally indicated by the numeral 1. A first aluminum substrate 2 is adhered about the periphery to a second plastics substrate 3 by use of an adhesive 4. A portion of aluminum substrate 2 is not adhered to plastics substrate 3 so as to provide release tabs 5a and 5b. Test material 6 containing a predetermined amount of analyte is disposed between aluminum substrate 2 and plastics substrate 3.

In use, release tab 5a is pulled in the direction of arrow B and release tab 5b is pulled in the direction of arrow C, thereby separating the substrates 2 and 3 and permitting access to test material 6.

A swab (not shown) is then wiped over surface 6. The amount of analyte present on the swab is then monitored using apparatus known to a person skilled in the art. The result obtained is then compared to the predetermined amount of analyte present on the first substrate so as to determine the accuracy of the swab technique.

While several particular forms of the invention have been illustrated and described, it will be apparent that various modifications can be made without departing from the spirit and scope of the invention.

We claim:

1. A device for use in monitoring a swab technique of an operator, comprising:
   a first substrate;
   a second substrate disposed adjacent the first substrate; and
   a test material disposed between the first substrate and the second substrate, the test material containing a predetermined amount of at least one test analyte, such that a swab thrust between the first and second substrate contacts the test material allowing transfer of a portion of the test analyte to the swab.

2. A device according to claim 1, wherein the at least one test analyte is selected from the group consisting of ATP, a protein, a chemical material a mineral, a sugar, a lipids, a fatty acid, a microbial cell wall, a cell membrane material, an enzyme and a micro organism.

3. A device according to claim 1, wherein the test material is protected from environment contamination prior to use.

4. A device according to claim 1, wherein the first substrate and the second substrate are sealed together substantially at their periphery so as to form a pouch or sachet, the test material being substantially contained in the pouch.

5. A device according to claim 4, wherein a bond is formed by use a method selected from the group consisting of using an adhesive, heat sealing the first substrate and the second substrate, or using a pressure sensitive adhesive.

6. A device according to claim 1 wherein the first substrate and the second substrate are coextrusion laminated.

7. A device according to claim 6, wherein at least one of the first substrate and the second substrate are formed from a material selected from the group consisting of ethylene vinyl acetate, ethylene methacrylate or ethylene vinyl alcohol.

8. A device according to claim 1, wherein the first substrate and the second substrate are manufactured from a material selected from the group consisting of metal and a plastics material.

9. A device according to claim 1, wherein the first substrate and the second substrate are formed from the same sheet of material.

10. A device according to claim 1, wherein the first substrate and the second substrate have respective internal surfaces which have different wetting properties such that the surface of the first substrate is more hydrophobic relative to the surface of the second substrate and the surface of the second substrate is more hydrophilic relative to the surface of the first substrate.

11. A device according to claim 10, wherein the test material disposed between the first substrate and the second substrate will preferentially wet the more hydrophilic surface leaving the more hydrophobic surface substantially unwetted.

12. A device according to claim 10, wherein the test material includes a hydrophilic surface enhancer which increases the probability of the test material wetting the more hydrophilic surface as opposed to wetting the more hydrophobic surface.

13. A device according to claim 1, wherein the test material includes a stabilizing agent.

14. A device according to claim 13, wherein the stabilizing agent includes a compound which reduces water availability therefore improving protein stability when the test material includes a protein.

15. A device according to claim 13, wherein the stabilizing agent is selected from the group consisting of a chelating agent, a quatenary ammonium detergent when the test material includes a micro-organism.

16. A device according to claim 1, wherein the test material includes a blend comprising:

| | |
|---|---|
| Glycerol | 50 g |
| Chlorhexidine gluconate | 2 g |
| Bovine serum albumin | 0.5 g |
| ATP | $0.18 \times 10^{-9}$ g and |
| De-ionized water | 50 g. |

17. A device according to claim 16, wherein the test material has a thickness on the first substrate less than about 1 mm.

18. A device according to claim 1, wherein the first substrate includes a first release portion and the second substrate includes a second release portion, each release portion being arranged about a peripheral edge of the respective substrate, the first release portion being substantially not connected to the second release portion.

* * * * *

UNITED STATES PATENT AND TRADEMARK OFFICE
CERTIFICATE OF CORRECTION

PATENT NO. : 7,297,530 B2 Page 1 of 1
APPLICATION NO. : 10/816659
DATED : November 20, 2007
INVENTOR(S) : Catherine Mary Ramsay It is certified that error appears in the above-identified patent and that said Letters Patent is hereby corrected as shown below:

Column 2
Line 5, Delete "calorimetric" and insert -- colorimetric --, therefor.
Line 38, Delete "(such" and insert -- such --, therefor.
Line 48, Delete "techoic" and insert -- teichoic --, therefor.
Line 61, After "of" delete "an" and insert -- a --, therefor.

Column 3
Line 4, Delete "methacylate" and insert -- methacrylate --, therefor.

Column 5
Line 61, In Claim 2, after "material" insert -- , --.
Line 61, In Claim 2, delete "a lipids," and insert -- a lipid, --, therefor.

Column 6
Line 4, In Claim 5, delete "use" and insert -- using --, therefor.
Line 17, In Claim 8, delete "plastics" and insert -- plastic --, therefor.
Line 45, In Claim 15, delete "quatenary" and insert -- quaternary --, therefor.

Signed and Sealed this

First Day of July, 2008

JON W. DUDAS
*Director of the United States Patent and Trademark Office*